United States Patent [19]
Sanford et al.

[11] Patent Number: 5,549,583
[45] Date of Patent: Aug. 27, 1996

[54] SURGICAL CONNECTOR

[75] Inventors: Adam Sanford, Colts Neck; John Cheer, Manasquan; James Wood, Oakhurst, all of N.J.

[73] Assignee: Adam Spence Corporation, Wall, N.J.

[21] Appl. No.: 511,471

[22] Filed: Aug. 4, 1995

[51] Int. Cl.[6] .................................................. A61M 25/00
[52] U.S. Cl. ......................... 604/283; 604/905; 285/921
[58] Field of Search ..................................... 604/283, 280, 604/243, 240, 905; 285/918, 921

[56] References Cited

U.S. PATENT DOCUMENTS

| | | |
|---|---|---|
| 115,917 | 6/1871 | Wharton .................................. 285/921 |
| 2,542,701 | 2/1951 | Press . |
| 2,560,263 | 7/1951 | Wiegand et al. . |
| 2,570,406 | 10/1951 | Troshkin et al. . |
| 2,893,395 | 7/1959 | Buck . |
| 2,963,304 | 12/1960 | Comlossy, Jr. et al. . |
| 3,503,385 | 3/1970 | Stevens . |
| 3,785,683 | 1/1974 | Adelhed . |
| 3,799,589 | 3/1974 | Boelkins . |
| 3,957,293 | 5/1976 | Rodgers . |
| 4,042,262 | 8/1977 | Mooney et al. . |
| 4,152,017 | 5/1979 | Abramson . |
| 4,254,773 | 3/1981 | Waldbillig . |
| 4,932,114 | 6/1990 | Morse et al. . |
| 5,047,021 | 9/1991 | Utterberg . |
| 5,125,915 | 6/1992 | Berry et al. .............................. 604/283 |
| 5,284,134 | 2/1994 | Vaughn et al. . |
| 5,312,377 | 5/1994 | Dalton . |

*Primary Examiner*—John D. Yasko
*Attorney, Agent, or Firm*—Oblon, Spivak, McClelland, Maier, & Neustadt, P.C.

[57] ABSTRACT

A connector which includes a female part having a barrel-shaped body, with a socket extending into the female part from one end of the barrel-shaped body. The socket includes first, second, and third step portions which respectively receive a flange, a shoulder, and a stem of a male part. A lip extends radially inwardly from the barrel-shaped body of the female part, with the lip having an inner diameter smaller than the outer diameter of the flange of the male part. The male part can be inserted into the female part by inserting the flange of the male part past the lip of the female part, such that the male and female parts are snapped together. In a presently preferred embodiment, a seal ring is disposed between the male and female parts, and the seal ring is compressed in an axial direction, thereby providing the connector with a fluid tight seal.

19 Claims, 2 Drawing Sheets

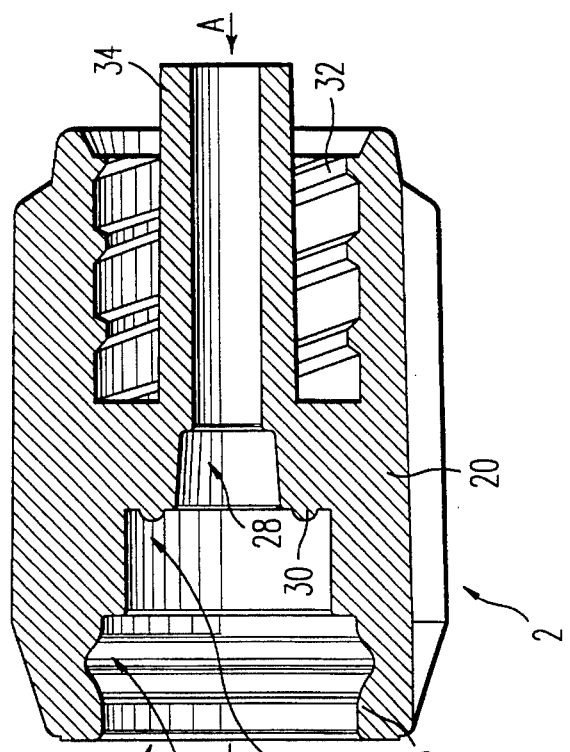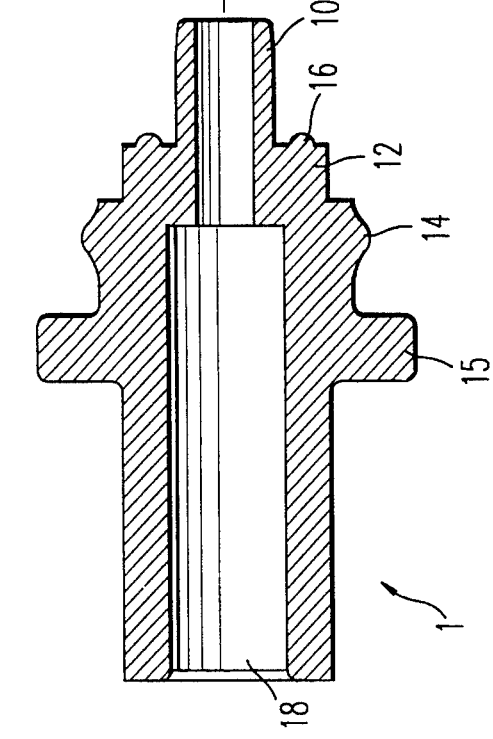

5,549,583

SURGICAL CONNECTOR

BACKGROUND OF THE INVENTION

1. Field of the Invention

This invention pertains to connectors, and particularly to surgical connectors utilized, for example, to connect a catheter to a fluid source. More particularly, the invention provides a connector which includes male and female Darts which are rotatable with respect to one another, while ensuring a fluid-tight coupling.

2. Background of the Invention

Swivel or rotatable coupling/connector devices are known as disclosed, for example, in U.S. Pat. No. 4,254,773 to Waldbillig. The Waldbillig coupling includes a collar forming a radially projecting portion on a female part, such that the female part receives a male part, with a loose fit between the male and female Darts. In addition, in Waldbillig, an O-ring is disposed between the male and female parts, and the male and female parts are axially spaced such that the O-ring is not axially compressed. While the Waldbillig collar and other structure which prevents axial O-ring compression results in a connector having male and female parts which are freely rotatable with respect to one another, the Waldbillig structure is less than optimal from a standpoint of maintaining a fluid-tight coupling, particularly when subjected to high fluid pressures. In fact, it is believed that the Waldbillig structure has not been practiced commercially.

As an alternative to the Waldbillig structure, an arrangement has been available (from the assignee of the Waldbillig patent) in which, in lieu of the collar structure, an end cap is fastened onto the female part (after insertion of the male part) to hold the male part in place. The cap is secured to the female part utilizing an adhesive or sonic welding. However, such an arrangement is disadvantageous due to the added sonic welding or adhering step, as well as the requirement for an additional cap component.

OBJECTS OF THE INVENTION

It is an object of this invention to provide a connector which avoids the aforementioned shortcomings.

It is another object of this invention to provide a connector which includes two pieces which are rotatable relative to one another, with a seal ring disposed between the two parts, and further with the seal ring axially compressed to ensure fluid tightness.

It is a further object of this invention to provide a connector which includes male and female parts which can be snapped together while also having sufficient structural integrity to withstand high fluid pressures.

It is a still further object of this invention to provide a connector which requires only three parts—i.e., a male part, a female part, and a seal ring.

SUMMARY OF THE INVENTION

The invention is a connector which includes a female part having a barrel-shaped body. A socket extends into the female part from one end of the barrel-shaped body, with the socket receiving a male part. The socket includes first, second, and third stepped portions. The first, second, and third stepped portions respectively receive a flange, a shoulder, and a stem of the male part. In addition, a lip extends radially inwardly from the barrel-shaped body of the female part. The lip has an inner diameter smaller than the outer diameter of the flange of the male part. The male part can be inserted into the female part by inserting the flange of the male part past the lip of the female part, such that the male and female parts are snapped together. Since the lip extends from the barrel-shaped body of the female part, a snap-together fit or snap-in lock is provided while also ensuring that the coupling can withstand high fluid pressures.

In a presently preferred embodiment, a seal ring is disposed between the male and female parts, and the seal ring is compressed in an axial direction, thereby improving the fluid tightness of the connector.

In accordance with another aspect of the presently preferred embodiment, a ridge is provided on at least one of the male and female parts, with the ridge(s) providing for axial compression of the seal ring while minimizing surface contact with the seal ring such that the male and female parts are rotatable with respect to one another.

BRIEF DESCRIPTION OF THE DRAWINGS

FIG. 1A is a cross-sectional view of the presently preferred embodiment of the male part of the connector of the invention.

FIG. 1B is a cross-sectional view of the presently preferred seal ring of the invention.

FIG. 1C is a cross-sectional view of the presently preferred embodiment of the female part of the present invention.

DETAILED DESCRIPTION OF THE PRESENTLY PREFERRED EMBODIMENT

Figure 3:
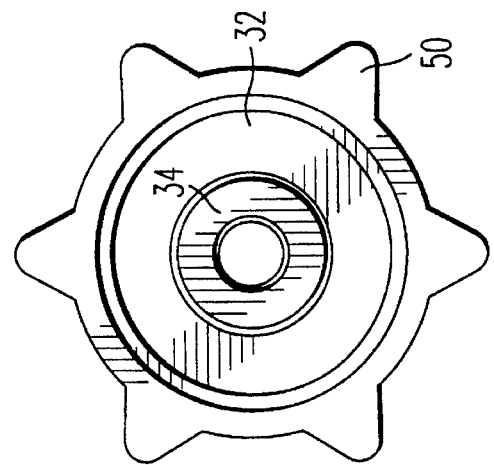
FIG. 3 is an end view of the female part of FIG. 1C, viewed from the direction of arrow A in FIG. 1C.

As shown in FIG. 1A, the presently preferred embodiment includes a stem 10, a shoulder 12, and a flange 14 on a male part 1. Preferably, the shoulder 12 includes a ridge or raised boss 16 which encircles the stem 10. The purpose of the shoulder or raised boss 16 is discussed hereinafter. In addition, the male part 1 includes an opening 18 to allow the male part 1 to be connected to a pressurized fluid source (not shown).

While the opening 18 is shown in the form of a recess which receives a tube, it is to be understood that other coupling arrangements are possible for the male part to allow the male part to be connected to a pressurized fluid source. It is also possible to provide the male part with a suitable connector to allow the male part to be connected to a catheter or other equipment (e.g., with the female part connected to the fluid source).

An additional flange or rim 15 is provided on the male part 1 to ease grasping of the male part 1 for insertion into a female part 2 and for manipulation (e.g., rotation) of the male part 1 with respect to the female part 2 after insertion.

The presently preferred form of the female part 2 (FIG. 1C) includes a barrel-shaped body 20 having a socket 22 which receives the male part 1. The socket 22 includes a first stepped portion 24, a second stepped portion 26, and a third stepped portion 28. As should be apparent from FIG. 1C, the stepped portions 24, 26, and 28 have progressively decreasing diameters. That is, the first stepped portion 24 has a larger diameter than the second stepped portion 26, and the third stepped portion 28 has a smaller diameter than the second stepped portion 26. Preferably, the second stepped portion 26 includes a ridge or boss 30 which, when the connector is assembled, faces the ridge 16 of the shoulder 12 of the male part 1.

The opposite end of the female part 2 (i.e., the end opposite to the end from which the socket 22 extends) includes an internally threaded Luer 32 and a tapered male Luer 34, such that the female part 2 can be connected to a catheter. As noted earlier, it is also possible to provide the female part 2 with a suitable connector to couple the female part 2 to a fluid source, with the male part 1 being connected to a catheter or other equipment. (Of course, the teachings of the present invention may be advantageously applied wherever it is desired to provide a fluid tight, rotatable joint.)

In accordance with one of the advantageous aspects of this invention, a lip 36 extends radially inwardly from the barrel-shaped body 20 of the female part 2. The lip 36 has an inner diameter smaller than the outer diameter of the flange 14 of the male part 1. The male part 1 and the female part 2 are preferably formed of a plastic material which is somewhat rigid, yet sufficiently yieldable to allow the flange 14 to be snapped past the lip 36, by yielding of one or both of the flange 14 and the lip 36. By providing the lip 36 as an extension from the barrel-shaped body 20 of the female part 2, the connector is better able to withstand high fluid pressures—e.g., as compared with the Waldbillig collar arrangement. (With a collar arrangement as provided by Waldbillig, fluid pressures can cause the radially projecting collar to yield, thus resulting in leakage or failure of the connector.) This invention is also advantageous in comparison to the welded cap type arrangement sold by Waldbillig's assignee, in that the additional cap component (and the sealing step therefor) is not needed.

FIG. 1B shows a seal ring which, in the presently preferred embodiment, is in the form of a quad ring 3. When the quad ring 3 is axially compressed, it expands radially, thus ensuring a fluid-tight seal between the male part 1 and the female part 2. As shown in FIG. 1B, the quad ring 3 includes grooves 3a, 3b. As discussed hereinafter, the ridge or raised boss 16 of the male part 1 and the ridge 30 of the female part 2 contact the quad ring 3 at the grooves 3a, 3b when the connector is in an assembled state.

Figure 2:
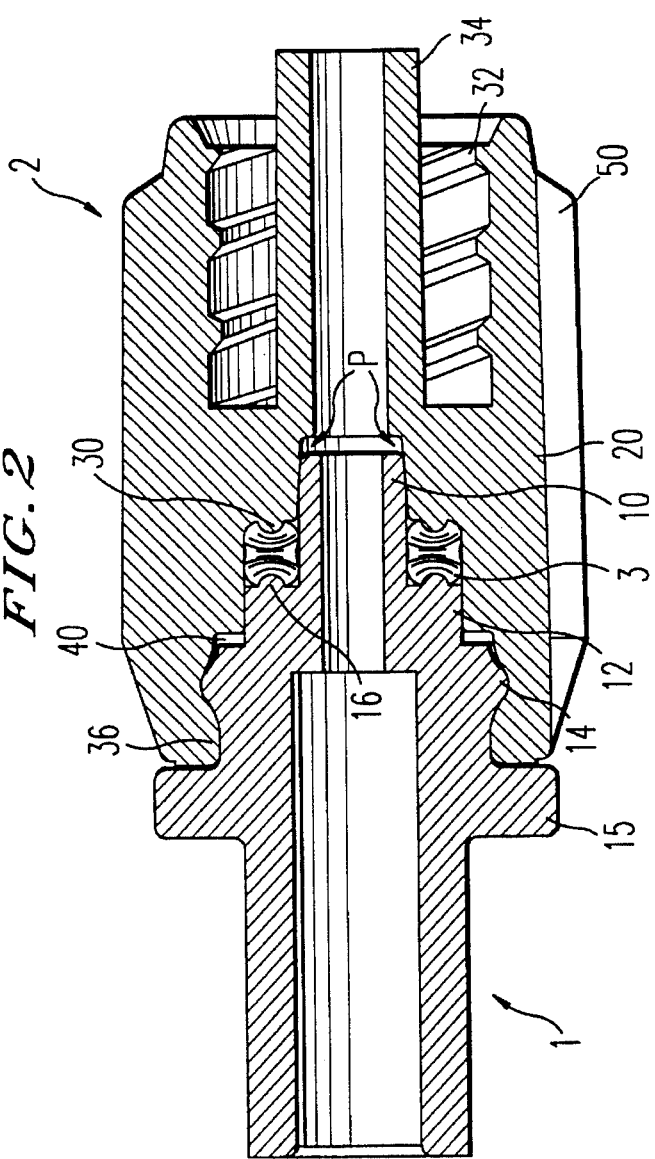
FIG. 2 is a cross-sectional view of the presently preferred embodiment of the invention with the parts in an assembled state and under pressure.

FIG. 2 shows the male part 1, the female part 2, and the quad ring 3, in an assembled state, with the connector also depicted in a pressurized condition. More particularly, when the connector is coupled to a pressurized fluid source, the male part 1 and the female part 2 are forced away from one another. Thus, in the assembled, under pressure state of FIG. 2, the flange 14 of the male part 1 is in the leftmost position (i.e., with respect to FIG. 2) as indicated by the space shown at 40. As shown in FIG. 2, even in this leftmost position, the ridge or raised boss 16 of the shoulder 12 of the male part 1 is sufficiently close to the ridge 30 of the female part 2 so that the quad ring 3 is axially compressed, thereby securing the quad ring 3 in place and compressing the quad ring 3 to ensure a fluid-tight seal.

As also shown in FIG. 2, the ridge or raised boss 16 of the male part 1 and the ridge 30 of the female part 2 contact the quad ring 3 at the grooves 3a, 3b to axially compress the quad ring 3. It is to be understood that other structures are possible for axially compressing a seal ring or quad ring. However, the ridged shoulder structure shown in FIG. 2 is presently preferred since it provides advantageous sliding/surface contact between the ridge or raised boss 16, the ridge 30, and the quad ring 3 such that the male part 1 and the female part 2 are rotatable with respect to one another, while also axially compressing the quad ring 3 for fluid tightness.

The ridge or raised boss 16 and the ridge 30 thus provide a small contact area with respect to the quad ring 3, thereby providing advantageous sliding movement upon the quad ring 3.

Of course, if desired, a ridge can be provided on only one of the male part 1 and the female part 2. In addition, a seal ring other than a quad ring may be utilized. However, the provision of ridges on both the male part 1 and the female part 2 in combination with the use of a quad ring is presently preferred.

As shown in FIG. 3, the female part 2 can include axially extending ridges 50 protruding from the barrel-shaped body 20 to assist in grasping and manipulating the female part 2.

CAVEAT

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters patent of the United States is:

1. A connector comprising:
   (a) a female part having:
      (i) a barrel-shaped body including a first end and a second end;
      (ii) a socket extending into the barrel-shaped body from said first end, said socket including a first stepped portion having a first diameter, a second stepped portion having a second diameter, and a third stepped portion having a third diameter, said first stepped portion being disposed closer to said first end than said second stepped portion, said second stepped portion being disposed closer to said first end than said third stepped portion, the diameter of said first stepped portion being larger than the diameter of said second stepped portion, and the diameter of said second stepped portion being larger than the diameter of said third stepped portion; and
      (iii) a lip extending radially inwardly from said barrel-shaped body of said female part at said first end and
   (b) a male part having:
      (i) a stem having an outer diameter and
      (ii) a flange having an outer diameter larger than the outer diameter of said stem,
   whereby:
   (c) in an assembled state, said stem is at least partially disposed in said third stepped portion and said flange is at least partially disposed in said first stepped portion.

2. A connector as recited in claim 1 wherein:
   (a) said lip has an inner diameter smaller than said outer diameter of said flange and
   (b) said flange is insertable past said lip to provide a snap-in connection between said male part and said female part.

3. A connector as recited in claim 1 further including a seal ring disposed in said second stepped portion.

4. A connector as recited in claim 3 wherein said seal ring is a quad ring.

5. A connector as recited in claim 3 further including a ridge disposed on one of said male part and said female part, said ridge contacting said seal ring when said connector is in said assembled state.

6. A connector as recited in claim 5 wherein:

(a) said seal ring includes a groove and (b) said ridge contacts said seal ring at said groove.

7. A connector as recited in claim 6 wherein said seal ring is a quad ring.

8. A connector as recited in claim 5 wherein:

(a) said male part is inserted into said female part in an axial direction and (b) in said assembled state, said seal ring is compressed in said axial direction between said male part and said female part.

9. A connector as recited in claim 5 wherein said ridge is disposed on said second stepped portion of said female part.

10. A connector as recited in claim 5 wherein:

(a) said male part further includes a shoulder disposed between said stem and said flange and (b) said ridge is disposed on said shoulder.

11. A connector as recited in claim 3 wherein:

(a) said male part further includes a shoulder disposed between said stem and said flange;

(b) said shoulder includes a first ridge projecting in an axial direction;

(c) said female part further includes a second ridge disposed on said second stepped portion;

(d) said second ridge projects toward said first ridge; and (e) said seal ring is disposed between said first ridge and said second ridge when said connector is in said assembled state.

12. A connector as recited in claim 11 wherein:

(a) said seal ring includes a first groove and a second groove and (b) in said assembled state, said first ridge contacts said seal ring at said first groove and said second ridge contacts said seal ring at said second groove.

13. A connector as recited in claim 12 wherein:

(a) said male part is inserted into said female part in an axial direction and (b) in said assembled state, said seal ring is compressed between said first ridge and said second ridge in said axial direction.

14. A connector as recited in claim 1 wherein:

(a) said male part is inserted into said female part in an axial direction and (b) the connector further includes a seal ring and means for compressing said seal ring in said axial direction when said connector is in said assembled state.

15. A connector comprising:

(a) a female part having:

(i) a first end and a second end and (ii) a socket extending into said female part from said first end, said socket including:

(A) a first stepped portion having a first diameter;

(B) a second stepped portion having a second diameter which is smaller than said first diameter; and (C) a third stepped portion having a third diameter which is smaller than said second diameter;

(b) a male part which is inserted into said female part in an axial directional, said male part having:

(i) a stem partially disposed in said second stepped portion and partially disposed in said third stepped portion of said female part, said stem extending through said seal ring;

(ii) a flange disposed in said first stepped portion of said female part; and (iii) a shoulder disposed between said stem and said flange, said shoulder being disposed in said second stepped portion of said female part;

(c) a seal ring disposed between a portion of said female part and a portion of said male part;

(d) means for providing a snap-in fit between said male part and said female part; and (e) means for compressing said seal ring in said axial direction ring comprising at least one ridge disposed on one of said shoulder and said second stepped portion.

16. A connector as recited in claim 15 wherein:

(a) said female part includes a barrel-shaped body; and (b) said means for providing a snap-in fit includes a radially inwardly extending lip disposed at said first end of said female part.

17. A connector as recited in claim 15 wherein:

(a) said female part further includes an opening extending from said second end into said female part; and (b) said opening includes an internal thread.

18. A connector as recited in claim 17 wherein said female part further includes a Luer connector protruding from said opening.

19. A connector as recited in claim 17 wherein:

(a) said female part has a barrel-shaped body and (b) said means for providing a snap together fit includes a lip extending radially inwardly from said barrel-shaped body.

\* \* \* \* \*